United States Patent
Faul et al.

(10) Patent No.: US 8,478,015 B2
(45) Date of Patent: *Jul. 2, 2013

(54) EXTENSION OF TRUNCATED CT IMAGES FOR USE WITH EMISSION TOMOGRAPHY IN MULTIMODALITY MEDICAL IMAGES

(75) Inventors: David Faul, Knoxville, TN (US); Christian J. Michel, Lenoir City, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/400,322

(22) Filed: Feb. 20, 2012

(65) Prior Publication Data

US 2012/0155736 A1 Jun. 21, 2012

Related U.S. Application Data

(60) Division of application No. 11/962,556, filed on Dec. 21, 2007, now Pat. No. 8,155,415, which is a continuation-in-part of application No. 11/428,456, filed on Jul. 3, 2006, now abandoned.

(60) Provisional application No. 60/696,307, filed on Jul. 1, 2005.

(51) Int. Cl.
*G06K 9/00* (2006.01)
*A61B 6/00* (2006.01)

(52) U.S. Cl.
USPC .............................................. 382/131; 378/4

(58) Field of Classification Search
None
See application file for complete search history.

(56) References Cited

U.S. PATENT DOCUMENTS

| | | | |
|---|---|---|---|
| 5,338,936 A * | 8/1994 | Gullberg et al. | 250/363.04 |
| 6,339,223 B1 | 1/2002 | Motomura et al. | |
| 6,810,102 B2 * | 10/2004 | Hsieh et al. | 378/4 |
| 6,950,493 B2 * | 9/2005 | Besson | 378/16 |
| 7,373,406 B2 * | 5/2008 | Jones et al. | 709/226 |
| 7,675,038 B2 * | 3/2010 | Ray et al. | 250/363.04 |
| 7,676,073 B2 * | 3/2010 | Hamill et al. | 382/128 |
| 7,737,406 B2 | 6/2010 | Vija et al. | |
| 2004/0030246 A1 * | 2/2004 | Townsend et al. | 600/427 |

* cited by examiner

*Primary Examiner* — Nancy Bitar
(74) *Attorney, Agent, or Firm* — Peter Kendall

(57) ABSTRACT

An apparatus and method for expanding the FOV of a truncated computed tomography (CT) scan. An iterative calculation is performed on the original CT image to produce an estimate of the image. The calculated estimate of the reconstructed image includes the original image center and a estimate of the truncated portion outside the image center. The calculation uses an image mask with the image center as one boundary.

11 Claims, 9 Drawing Sheets

EXTENSION OF TRUNCATED CT IMAGES FOR USE WITH EMISSION TOMOGRAPHY IN MULTIMODALITY MEDICAL IMAGES

CROSS-REFERENCE TO RELATED APPLICATION AND CLAIM FOR PRIORITY

This application is a divisional application of U.S. patent application Ser. No. 11/962,556 filed on Dec. 21, 2007, the disclosure of which is incorporated by reference in its entirety

BACKGROUND OF THE INVENTION

1. Technical Field

The present invention relates generally to medical diagnostic imaging and to use of medical images in one imaging modality with medical images from another imaging modality. More specifically the invention relates to extension or extrapolation of image data from a Computed Tomography (CT) transmission scan having a limited Field of View (FOV) so as to extend the CT image to a larger FOV. The FOV extension increases the anatomic information provided by the CT scan, and it makes the attenuation data provided by the CT image more accurate for correcting radionuclide emission data obtained from an emission computed tomography scan such as Positron Emission Tomography (PET) or Single Photon Emission Computed Tomography (SPECT). In particular, the invention relates to the use of a process, which could be iterative, for reconstruction of a CT image from transmission image data. This process compensates for missing transmission data from an extended FOV outside the CT measurement field. This extended FOV could be associated with that part of the FOV of a corresponding PET or SPECT scan of the same region that lies outside the CT FOV. The extended CT data can be used, for example, to generate attenuation correction factors for the corresponding PET or SPECT data, as well for reconstruction of CT images for co-registration with PET or SPECT reconstructed images.

2. Description of the Related Art

Single Photon Emission Computed Tomography (SPECT), Positron Emission Tomography (PET), and Computed Axial Tomography (CT) are three medical imaging modalities. SPECT, PET, and CT are popular in medicine because of their ability to non-invasively study both physiological processes and structures within the body. To better utilize SPECT, PET and CT, recent efforts have been made to combine either a SPECT scanner with a CT scanner or a PET scanner with a CT scanner into a single system. The combination of SPECT and CT or of PET and CT allows for better registration of the metabolic or functional SPECT and PET images with the anatomic CT image and for improved hospital workflow. The combined scanners share space within the same system housing and share a common patient bed or gurney, but use separate detectors and associated hardware. In the case of the PET/CT scanner see, for example, U.S. Pat. No. 6,449,331, issued to Nutt, et al., on Sep. 10, 2002, entitled "Combined PET and CT Detector and Method for Using Same," which discloses a combined PET and CT scanner, and which is incorporated herein by reference in its entirety.

SPECT and PET are nuclear medicine imaging techniques used in the medical field to assist in the diagnosis of diseases. In both cases medical images are regenerated based on radioactive emission data, typically in the form of gamma rays, emitted from the body of a patient after the patient has ingested or been injected with a radiopharmaceutical substance. SPECT and PET allow the physician to examine large sections of the patient at once and produce pictures of many functions of the human body unobtainable by other imaging techniques. In this regard, SPECT and PET display images of how the body works (physiology or function) instead of simply how it looks (anatomy or structure).

Mechanically, a SPECT or PET scanner consists of a bed or gurney and a gantry, which is typically mounted inside an enclosure with a tunnel through the center, through which the bed traverses. The patient, who has been infused with a radiopharmaceutical, lies on the bed, which is then inserted into the tunnel formed by the gantry. The gantry is rotated (either physically or electronically simulated with a stationary ring) around the patient as the patient passes through the tunnel. The rotating gantry contains the detectors and a portion of the processing equipment.

In the case of SPECT, emitted gamma rays are detected from numerous different projection angles by a gamma camera (a.k.a. Anger camera or scintillation camera) about a longitudinal axis of the patient, and converted into electrical signals that are stored as image data. Data from image projections provide a set of images as a result of a process known as image reconstruction. In the case of PET, the scanner detectors are designed to detect simultaneous and oppositely traveling gamma ray pairs from positron annihilation events within the patient. The injected or ingested radiopharmaceutical contains positron-emitting atoms. The positrons annihilate with electrons in the patient to produce pairs of gamma rays where each member of the pair moves in an opposite direction. The paired gamma rays generate signals when they strike the PET scanner detectors. Signals from the gantry are fed into a computer system where the data is then processed to produce images as a result of a process known as image reconstruction.

PET is considered the more sensitive of the two nuclear medicine imaging techniques, and exhibits the greatest quantification accuracy, of any nuclear medicine imaging instrument available at the present time. Applications requiring this sensitivity and accuracy include those in the fields of oncology, cardiology, and neurology.

Another known tomography system is computed axial tomography (CAT, or now also referred to as CT, XCT, or x-ray CT). In CT, an external x-ray source is caused to be passed around a patient. Detectors on the other side of the patient from the x-ray source then respond to the x-ray transmission through the patient to produce an image of the area of study. Unlike SPECT or PET, which are emission tomography techniques because they rely on detecting radiation emitted from inside the patient, CT is a transmission tomography technique which utilizes a radiation source external to the patient. CT provides images of the internal structures of the body, such as the bones and soft tissues, whereas SPECT and PET provide images of the functional aspects, such as metabolism, of the body, usually corresponding to an internal organ or tissue.

Unlike the pairs of PET scanner detectors required to detect the gamma ray pairs from an annihilation event or the detector heads of the SPECT scanner, the CT scanner requires detectors mounted opposite an x-ray source. In third-generation computed tomography systems, the CT detectors and x-ray source are mounted on diametrically opposite sides of a gantry which is rotated around the patient as the patient traverses the tunnel.

The x-ray source emits a beam of x-rays which pass through the patient and are received by an array of detectors. As the x-rays pass through the patient, they are absorbed or scattered as a function of the densities of objects in their path.

The output signal generated by each detector is representative of the x-ray attenuation of all objects between the x-ray source and the detector.

The medical images provided by the SPECT/CT scanner or by the PET/CT scanner are diagnostically complementary, and it is advantageous medically to have images of the same region of a patient from both emission and transmissions scans. To be most useful, the SPECT and CT images or the PET and CT images need to be correctly overlaid or co-registered such that the functional features in the PET images can be correlated with the structural features, such as bones, tumors, and lung tissue, in the CT images. The potential to combine functional and anatomical images is a powerful one, and there has been significant progress in the development of multi-modality image co-registration and alignment techniques. However, with the exception of the brain, the co-alignment of images from different modalities is not straightforward or very accurate, even when surface markers or reference points are used. To this end, it is desirable to incorporate SPECT and CT scanners or PET and CT scanners into a single gantry, thereby allowing the image data to be acquired sequentially or possibly simultaneously within a short period of time on the same patient table and overcoming alignment problems due to patient movement or internal organ movement such as caused by cancer treatment, respiration, variations in scanner bed profile, positioning of the patient for the scan, and other temporal changes in the patient.

SPECT and PET image reconstruction methods include iterative methods, such as ART (Algebraic Reconstruction Technique), EM (Expectation Maximization), ML (Maximum Likelihood), OSEM (Ordered Subset Expectation Maximization), and MAP (Maximum A Posteriori), as well as traditional (non-iterative) reconstruction methods, such as filtered back-projection (FBP). (OSEM is a modified EM technique based on ordered subsets.) Iterative reconstruction methods often provide better image quality and more natural ways to incorporate attenuation correction than non-iterative methods. However, iterative methods are generally more computationally intensive and more time-consuming than non-iterative methods. In fact, iterative techniques can be on the order of ten times slower than non-iterative techniques. Consequently, in the past iterative techniques were not used in CT as sufficient computational power was cost prohibitive for the resolution and contrast requirements of that modality.

Over a period of approximately fifteen years a number of studies have addressed attenuation correction of SPECT or of PET emission images obtained using transmission images reconstructed with tomographic techniques. According to U.S. Pat. No. 5,376,795, photon attenuation constitutes a major deficiency in diagnosis of heart disease with SPECT and is a major source of error in the measurement of tumor metabolism using radionuclide techniques. A number of researchers have shown that transmission imaging techniques can be used to create attenuation maps that can be used to correct photon attenuation in emission image data. These techniques include CT.

An example of the prior art in attenuation correction for emission computed tomography with transmission computed tomography is U.S. Pat. No. 6,339,652, titled, "Source-assisted attenuation correction for emission computed tomography." This patent describes a method of ML-EM image reconstruction that is provided for use in connection with a diagnostic imaging apparatus that generates projection data. The method includes collecting projection data, including measured emission projection data and measured transmission projection data. Optionally, the measured transmission projection data is truncated. An initial emission map and attenuation map are assumed. The emission map and the attenuation map are iteratively updated. With each iteration the emission map is recalculated by taking a previous emission map and adjusting it based upon: (i) the measured emission projection data; (ii) a re-projection of the previous emission map which is carried out with a multi-dimensional projection model; and, (iii) a re-projection of the attenuation map. As well, with each iteration the attenuation map is re-calculated by taking a previous attenuation map and adjusting it based upon: (i) the measured emission projection data; (ii) a re-projection of the previous emission map which is carried out with the multi-dimensional projection model; and (iii) measured transmission projection data.

Other studies in this area include disclosures of U.S. Pat. No. 5,739,539, which describes a method of performing image reconstruction in a gamma camera (SPECT) system that includes the steps of performing a transmission scan of an object about a number of rotation angles to collect transmission projection data and performing an emission scan of the object about numerous rotation angles to collect emission projection data. The outer boundary of the object is then located based on the transmission projection data. Information identifying the boundary is then either stored in a separate body contour map or embedded in an attenuation map. Information identifying the boundary can be in the form of flags indicating whether individual pixels are inside or outside the boundary of the object. The emission projection data is then reconstructed using the attenuation map, if desired, to generate transverse slice images. Image reconstruction requires less time if the process ignores pixels outside the body boundary.

U.S. Pat. No. 6,856,666 describes multi-modality imaging methods and apparatus for scanning an object in a first modality, having a first field of view to obtain first modality data including fully sampled field of view data and partially sampled field of view data. The method also includes scanning the object in a second modality having a second field of view larger than the first field of view to obtain second modality data, and reconstructing an image of the object using the second modality data and the first modality partially sampled field of view data.

U.S. Pat. No. 6,140,649 titled "Imaging attenuation correction employing simultaneous transmission/emission scanning," describes a nuclear medical imaging system generates transmission and emission images simultaneously. The system includes a gamma camera and a linear transmission source disposed on opposite sides of an imaging region in which a patient lies. A plurality of views is taken at different rotational angles around a patient. At each angle, the view acquisition period is divided into two segments based on whether the transmission source is on or off. Emission image data is acquired either in both period segments or only while the transmission source is off. The transmission image data is acquired when the transmission source is on, and crosstalk image data is acquired when the transmission source is off.

U.S. Pat. No. 5,338,936 titled "Simultaneous transmission and emission converging tomography," describes a SPECT system that includes three gamma camera heads which are mounted to a gantry for rotation about a subject. The subject is injected with a source of emission radiation, which emission radiation is received by the camera heads. Transmission radiation from a transmission radiation source is truncated to pass through a central portion of the subject but not peripheral portions and is received by one of the camera heads concurrently with the emission data. As the heads and radiation source rotate, the transmitted radiation passes through different parts or none of the peripheral portions at different angular orientations. An ultrasonic range arranger measures an actual periphery of the subject. Attenuation properties of the subject are determined by reconstructing the transmission data using an iterative approximation technique and the measured actual subject periphery. The actual periphery is used in the reconstruction process to reduce artifacts attributable to radiation truncation and the associated incomplete sampling of the peripheral portions. An emission reconstruction processor reconstructs the emission projection data and attenuation properties into an attenuation corrected distribution of emission radiation sources in the subject.

Each improvement in co-registration of multimodality image data and attenuation correction of nuclear medicine images provides benefits associated with the quality of medical diagnoses. For this reason there is continuing need for methods of image reconstruction for reliable reproduction of a patient's physical and functional condition.

One limitation of attenuation maps created by CT transmission data is the relatively small usable FOV (typically on the order of 50 cm diameter) compared to the FOV of a PET scanner (typically on the order of 70 cm diameter or more). Often the patient's arms are truncated in the CT image because they extend beyond the CT FOV. Also, patients positioned off-center on the bed or obese patients may have a portion of their body truncated for the same reason. Various methods have been developed to reconstruct and extend the FOV of CT images. However, for various reasons, these attempts either do not extend the FOV far enough or introduce artifacts and/or distortion in the images.

Current methods for extending the FOV of CT consist of extrapolating the projection data into the truncated region and reconstructing the image from the extrapolated data by variants of the convolution/back projection (or filtered back projection) reconstruction technique. Prior art methods for reconstructing CT images to extend the FOV are known from the literature. However, these prior art methods have proven unacceptable for reconstructing truncated views.

A representative example of the prior art is an article titled "A novel reconstruction algorithm to extend the CT scan field-of-view," authored by J. Hsieh, et al., published in the journal Med. Phys. 31(9) September, 2004. This article discloses a reconstruction algorithm that makes use of the fact that the total attenuation of each ideal projection in a parallel sampling geometry remains constant over views. The magnitudes and slopes of the projection samples at the location of truncation are used to estimate the projection data outside the scan field of view.

Another example of the prior art is an article titled "Efficient correction for CT image artifacts caused by objects extending outside the scan field of view," authored by B. Ohnesorge, et al., published in the journal Med. Phys. 27(1), January, 2000. This article discloses a method of eliminating CT image artifacts generated by objects extending outside the scan FOV. The abstract states: "CT projection data are measured only within the scan field of view and thus are abruptly discontinuous at the projection boundaries if the scanned object extends outside the scan FOV. This data discontinuity causes an artifact that consists of a bright peripheral band that obscures objects near the boundary of the scan FOV. An adaptive mathematical extrapolation scheme with low computational expense was applied to reduce the data discontinuity prior to convolution in a filtered back projection reconstruction."

SUMMARY OF THE INVENTION

According to one embodiment of the present invention, an apparatus and method for extending or expanding the field of view (FOV) of a computed tomography (CT) scan is provided. The FOV extension system includes a technique for extending the CT image to regions beyond the FOV. The FOV extension system uses one or more masks to determine the data to be used in the calculation. In the simplest embodiment the mask extends from an inner boundary around the image center, which encompasses a large part of the object within the CT FOV, to an outer boundary encompassing truncated portions of an imaged object. The technique uses the reconstructed CT image data within the inner boundary of the mask without change and extends the reconstructed CT image to areas outside the mask and, further, to areas outside the CT scanner FOV.

In another embodiment of the present invention, the mask used in the process described herein is reduced in area. The truncated mask excludes additional areas from CT image extension such as the region below the lowest point of the reconstructed object and the region above the highest point of the reconstructed object in the FOV. In yet another embodiment of the present invention, the method for extending the FOV can be improved if the CT system is part of a combined PET/CT scanner or SPECT/CT scanner. In this embodiment, the outer boundary of the mask is determined from SPECT or PET images whose axial positions corresponding to those of the CT images. This invention reduces the computation time for the extension of the CT image FOV and improves the accuracy with respect to the prior art of CT images in the region of extension. The improved CT images, in turn, improve the accuracy of the PET and SPECT attenuation correction with respect to the prior art.

BRIEF DESCRIPTION OF THE DRAWINGS

The above-mentioned features of the invention will become more clearly understood from the following detailed description of the invention read together with the drawings in which.

DETAILED DESCRIPTION OF THE INVENTION

Figure 1A:
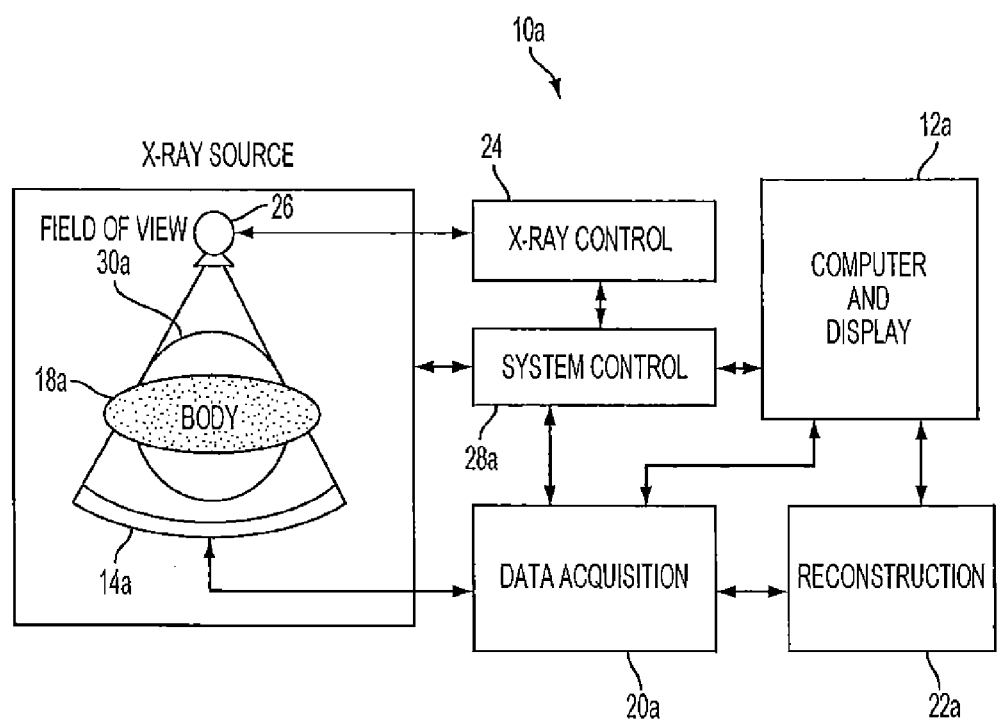
FIG. 1A is a schematic diagram of an exemplary computed tomography (CT) imaging system as contemplated by the present invention.

As required, disclosures herein provide detailed embodiments of the present invention; however, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

A process according to the present invention uses an imaging system as a means to reveal the presence of defects in the structures, organs or tissues of a patient who exhibits symptoms of an undesirable condition. The imaging system first requires that the patient adopt a position for collection of data from the organ or area of tissue under study, also referred to herein as the imaged object. The process in accordance with the invention can be used to extend the FOV of a computed tomography (CT) scanner in either standalone applications, to extend a usable CT image, or in multimodality imaging applications, to provide extended attenuation correction information. Thus, in one embodiment of the invention, data collection proceeds using a system that acquires transmission data and processes the data into images to be stored and/or displayed on a monitor or a flat screen display. In another embodiment of the invention, data collection proceeds using a dual modality technique that may include either simultaneous or sequential acquisition of transmission signals and emission signals for sensing by detectors that provide data to a computer. The computer processes the data into images to be stored and/or displayed on a monitor or a flat screen display.

Generally, during transmission scanning, a source of known radiation, e.g. x-rays, passes through a patient at known radiation intensity. Measurement of the intensity of radiation detected at different projection angles provides information of the extent of radiation attenuation over different spatial locations. From this information, a non-uniform attenuation map of the body and nearby structures may be generated using well known methods and procedures, including filtered back-projection (FBP) reconstruction techniques, for example.

The non-uniform attenuation map, applied during the reconstruction of emission projection data, corrects emission image data for more accurate display of the imaged object obtained from the emission modality.

In one embodiment according to the present invention, devices suitable for image data collection include a CT device operating in transmission mode to collect anatomical data and a nuclear medicine (NM) imaging device such as a single photon emission computed tomography (SPECT) scanner or a positron emission tomography (PET) scanner for collecting functional data. For example, among the many CT devices that may be used is a digital x-ray CT device. Using such a digital x-ray CT device, a beam of x-rays impinges on a detector that uses an active matrix of x-ray radiation detectors to convert the transmitted x-rays at a given position within the matrix into a signal that is a monotonically increasing function of the x-ray energy at that point. The detector converts x-ray signals into electrical signals that are amplified and digitized for processing into images.

Since the imaging system according to the present invention requires patient positioning before collection of image data, there is a high probability that the patient will be in a position that remains consistent during the CT and PET or SPECT portions of image data acquisition, greatly simplifying the process of correlating and fusing the anatomic information presented in the CT image and the functional information presented in the PET or SPECT image. This also allows the CT image to provide attenuation correction information for the reconstruction of the PET or SPECT images, excluding that portion of the PET or SPECT images corresponding to where the patient extends beyond the CT FOV.

Some multi-modality systems have different fields of view (FOVs) for the different modalities. For example, a CT system that is part of a CT/PET system, according to the present invention, might have a CT FOV which is smaller than the PET FOV, and, under some scanning conditions, portions of a patient imaged by the PET apparatus may extend beyond the region measured by the x-ray CT detector. Missing transmission data caused by truncation of the CT image leads to image artifacts and incomplete representations of the imaged object, as there is insufficient transmission data to provide accurate attenuation correction for the SPECT or PET images in the truncated areas.

An apparatus and system for expanding the FOV of a computed tomography (CT) scan is provided by the present invention. This process estimates the missing transmission data, which can be used to reconstruct the CT image to the full FOV, and which also can be used, for example, in attenuation correction of the emission data. The FOV extension system manipulates the CT image data to reconstruct at least a portion of the image truncated by the FOV of the CT scanner.

Figure 1B:
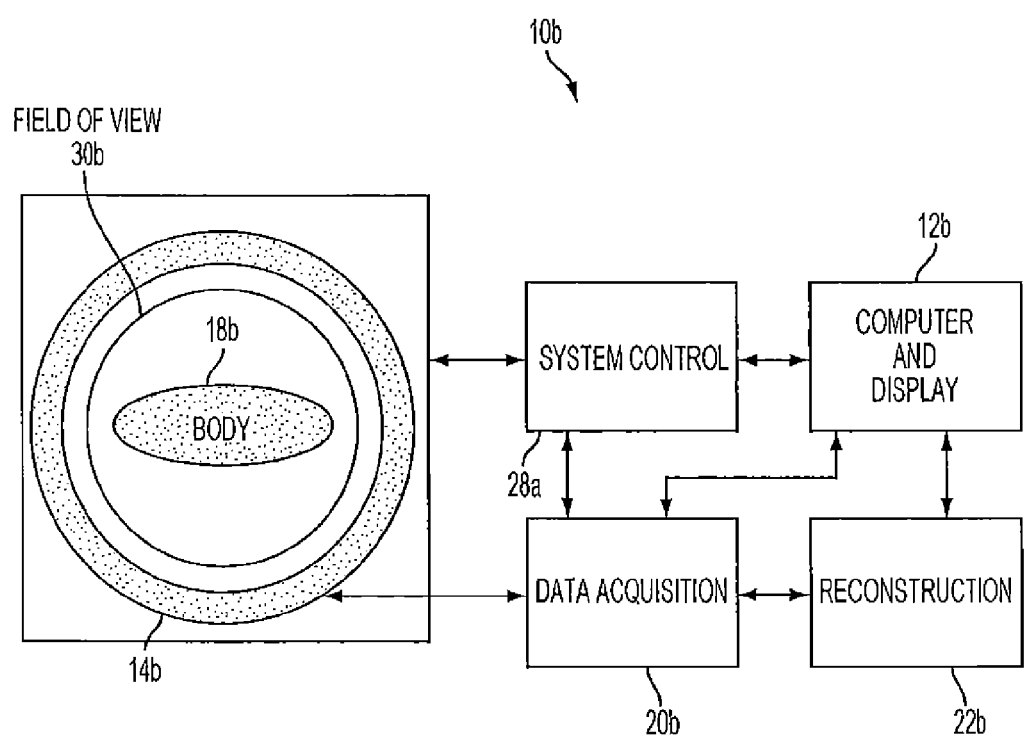
FIG. 1B is a schematic diagram of an exemplary emission imaging system as contemplated by the present invention.

Further description of the present invention refers to the drawings in which FIG. 1A and FIG. 1B are schematic diagrams of exemplary imaging systems. FIG. 1A illustrates a standalone CT device $10a$ and FIG. 1B illustrates a PET or SPECT device $10b$, suitable for use together with CT device $10a$ according to the present invention. The systems include general purpose computers $12a$ and $12b$ to store image data and to process image information supplied from a detector $14a$ that detects transmission radiation from source $26$ through imaged object $18a$ and a detector $14b$ that detects coincidence photon events in the case of PET or single photon events in the case of SPECT emitted by the imaged object $18b$, which is, at least, a portion of a patient's body. Signal processing hardware includes data acquisition devices $20a$ and $20b$ and image reconstruction units $22a$ and $22b$ for connecting the detectors $14a$ and $14b$ to the computers $12a$ and $12b$, to supply transmission or emission data for reconstruction into images of the imaged object $18$. The computers $12a$ and $12b$ control the imaging equipment, during scanning, using an x-ray control $24$ for the x-ray source $26$ and system controls $28a$ and $28b$ for movement of the detectors $14a$ and $14b$ in the case of SPECT on a gantry (not shown), or PET having only a pair of detectors, as they rotate, mechanically or electronically, about an axis corresponding to the longitudinal axis of the patient. Using data acquired from the detectors $14a$ and $14b$, a computing routine provides projection data for storage, in matrix form, within the memory of the computers $12a$ and $12b$.

In some applications, the emission and transmission imaging systems $10a$ and $10b$ might be conjoined rather than separate and the emission imaging system might be non-rotating, as would be the case for PET imaging systems with ring detectors.

For those cases in which information from the CT scanner $10a$ is made available to the PET or SPECT scanner $10b$ and the CT image processor $22a$ communicates with the PET or SPECT image processor $22b$, the PET or SPECT scanner uses the CT information to develop an attenuation correction for emission image reconstruction. The better the attenuation correction in PET or SPECT, the better is the PET or SPECT image representation of the tracer uptake. The CT scanner does not produce any attenuation information outside the CT FOV $30a$. In one embodiment of the present invention, the CT image processor $22a$ performs the processing on the CT data to expand the CT FOV beyond the area enclosed by 30a as shown in FIG. 1A. The expanded FOV information is then communicated to the PET or SPECT scanner 10b for use by the PET or SPECT scanner in developing attenuation information. In another embodiment, the PET or SPECT scanner 10b receives the CT data and the PET or SPECT image processor 22b performs the processing on the CT data to expand the FOV.

Although the illustrated embodiments are disclosed as working with a CT scanner 10a and a PET or SPECT scanner 10b as shown in FIGS. 1A and 1B, the invention is not so limited. In another embodiment, the technique is usable with CT systems that employ flat panel detectors where the expanse of the flat panel limits the FOV.

Figure 2:
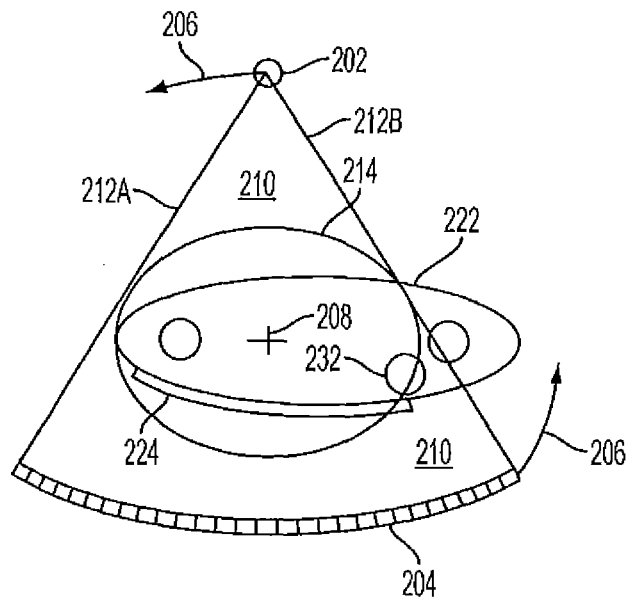
FIG. 2 is a diagram showing the limited field of view (FOV) of a CT scanner.

FIG. 2 shows an example of the limited FOV 214 of a CT scanner 10a, having a source 202 that produces a fan beam 210 of x-rays. The CT scanner further includes an array of x-ray detectors 204. Source 202 and detector array 204 are mounted on a gantry (not shown) for rotation in the same direction 206 about a central axis 208. The x-ray source 202 emits a fan beam of radiation 210 that is detected by the detectors in array 204. Lines 212A and 212B delineate the boundaries of the fan beam 210. Patient 222 lies on a patient bed 224, between the x-ray source 202 and detector array 204, such that the fan beam 210 passes through the patient 222 and the radiation emitted from the opposite side of the patient adjacent to the detector array 204 contains information about the internal structure of the patient. As the x-ray source 202 and detector array 204 rotate about the axis of rotation 208, the boundaries 212A and 212B remain tangent to circle 214, which thus defines the FOV of the CT scanner. As shown, there may exist significant portions of the patient 222 that remain outside the FOV 214 of the CT scanner as the CT scanner rotates about the patient, and which portions (which may include an organ or other region of interest 232 having one section in the FOV and another section outside of the FOV) therefore are not fully imaged by the CT scanner, in the sense that complete projection data from all angles is not obtained for such portions.

Figure 3A:
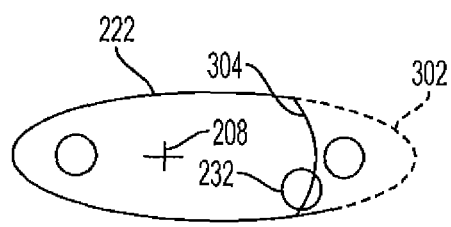
FIG. 3A is a diagram illustrating a region of a scanned subject outside the limited FOV of the CT scanner.

FIG. 3A illustrates a region 302 of the patient 222 that lies outside the FOV 214 of the CT scanner. While it is desired for a patient to be centered in the FOV, as shown in FIG. 2 it is possible for the patient 222 to be offset with respect to the axis of rotation 208; it is also possible for the patient to extend outside the FOV due to extended girth or to have arms extend outside the FOV. In such cases, image data obtained from portions of the patient outside the FOV, such as portion 302, is truncated. Such portions may include regions of interest (ROI) such as ROI 232, which lies partly inside the FOV and partly outside the FOV. Consequently, the part of the reconstructed CT image bounded by the ROI 232 typically is distorted and/or contains artifacts, such that its usefulness for diagnostic or attenuation correction purposes is diminished or non-existent, when the CT image is reconstructed according to prior art techniques.

Figure 3B:
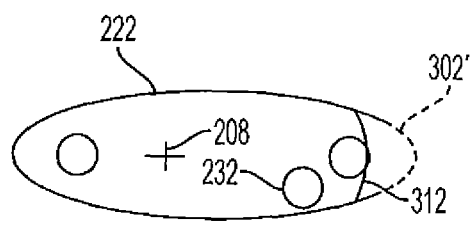
FIG. 3B is a diagram illustrating the expansion of the effective FOV of the CT scanner in accordance with an embodiment of the invention.

FIG. 3B shows an expanded effective FOV obtained in accordance with the present invention. As shown, according to the invention the effective FOV of the CT scanner is extended or expanded from boundary 304 as shown in FIG. 3A, to extended boundary 312. Thus, while there may remain a portion 302' of the patient that still remains outside the extended FOV, the effective FOV has been expanded so that ROI 232 is now fully within the FOV and can be reconstructed without distortion or artifact.

It bears noting that the portion of the CT image near the truncation boundary 304, 312 is subject to distortion and/or artifacts because the truncated portion 302 and 302' of the patient 222 is not always within the view of the detectors 204 as the source 202 and detectors 204 rotate about the patient 222. For example, with the source 202 and detectors 204 positioned as illustrated in FIG. 2, a portion of the patient 222 is outside the boundary line 212B of the fan of radiation 210 and, consequently, that portion is not seen by the detectors 204. With the source 202 and detectors 204 rotated 90° from the position illustrated in FIG. 2, the patient 222 is totally enclosed in the fan of radiation 210 from the source 202, and therefore the portion of the patient 222 not imaged at the first rotational position of the source and detectors will be imaged at this rotational position of source and detectors. This portion of the patient therefore will have image data for only some, but not all projection angles of the source and detectors, thereby resulting in distortion and/or artifacts.

Figure 4:
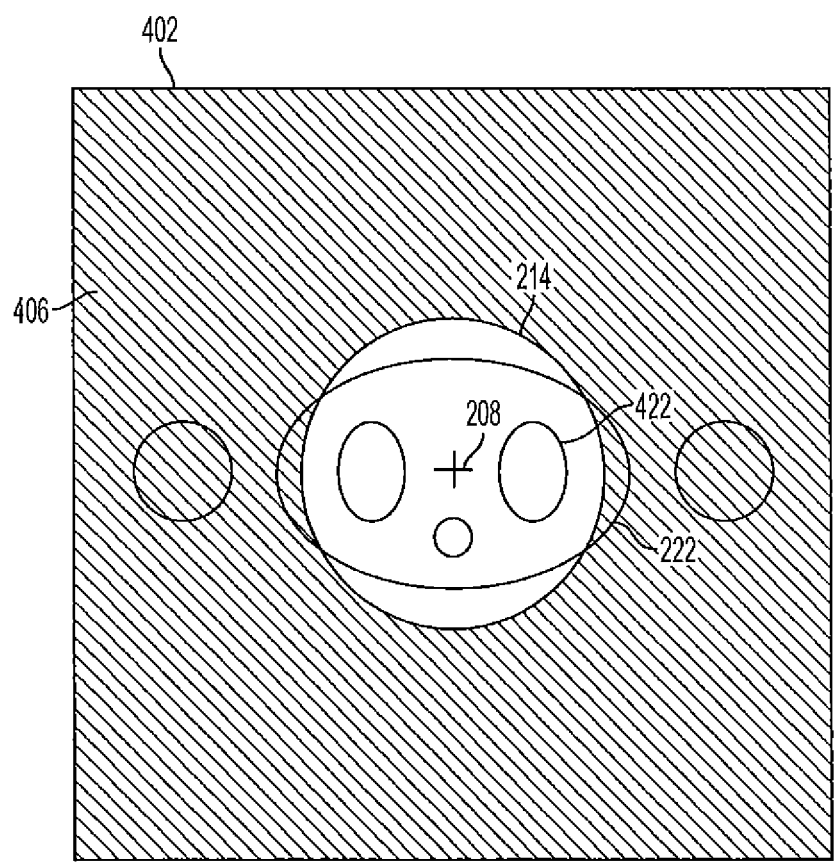
FIG. 4 shows one embodiment of a CT image reconstruction mask in accordance with the invention.

FIG. 4 is a pictorial view of one embodiment of a CT image reconstruction mask 402. The illustrated image reconstruction mask 402 consists of a square that encloses the CT scanner FOV 214, which contains a non-truncated portion 422 of the patient 222. In the illustrated embodiment, the patient 222 is larger than the FOV 214 of the scanner 10a and is centered about the center of rotation 208, wherein the non-truncated portion 422 is the portion of the patient 222 within the FOV 214 of the scanner 10a. By limiting the reconstruction task to the area of interest 406 (i.e., the area of mask 402 excluding FOV 214), the computational overhead is reduced compared to the reconstruction task for computing the entire image within the outer boundary of mask 402. In another embodiment of this invention, the inner boundary of mask 402 can lie within the boundary of the CT scanner FOV 214, in other words, the mask 402 can mask more than areas outside the FOV 214. Consequently, hereinafter area 214 will be referred to as the "image center," which may encompass the CT FOV or less than the CT FOV.

Figure 5:
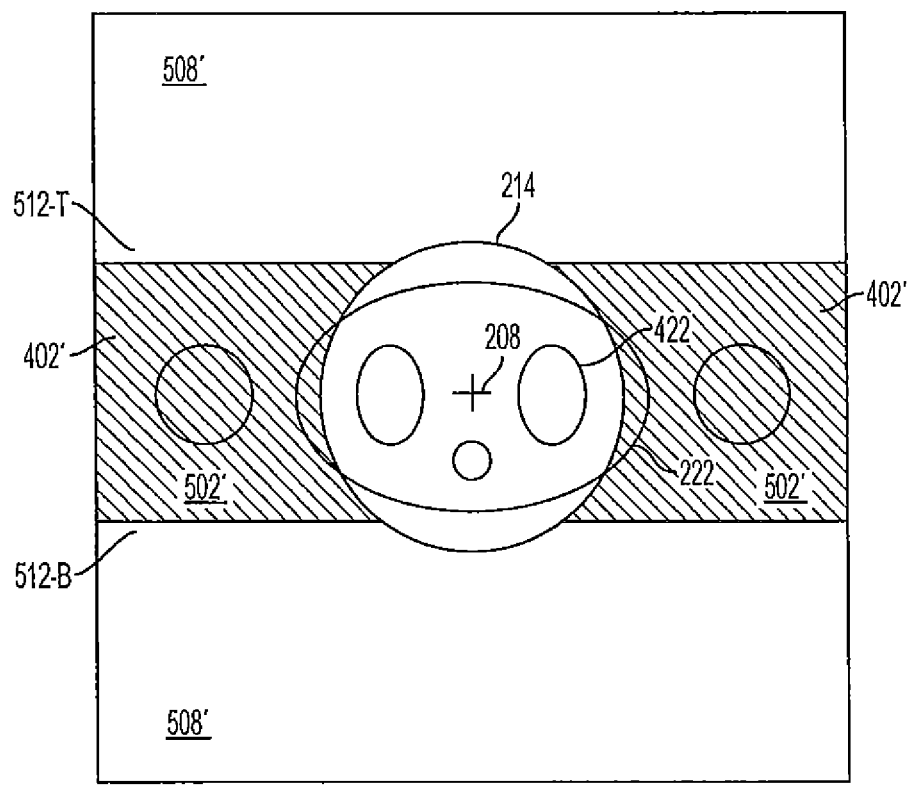
FIG. 5 shows another embodiment of a CT image reconstruction mask in accordance with the invention.

FIG. 5 is a pictorial view of another embodiment of a CT image reconstruction mask 402'. This embodiment of the image reconstruction mask 402' includes areas of interest 502 and areas of no interest 508. The areas of interest 502 encompass the truncated portions 302 of the patient 222 as shown in FIG. 3A and the area immediately surrounding those areas 302 as shown in FIG. 3A. By limiting the reconstruction mask to the areas of interest 502, the computational overhead is reduced further compared to the reconstruction mask 402 illustrated in FIG. 4.

The side boundaries of the reconstruction mask 402' illustrated in FIG. 5 extend from the sides of the image center 214 to areas beyond the boundaries of the patient 222. The top and bottom boundaries 512-T, 512-B of the reconstruction mask 402' illustrated in FIG. 5 do not extend past the top and bottom, respectively, of the patient 222. The top and bottom boundaries 512-T, 512-B of the reconstruction mask 402', in one embodiment, are fixed at a position determined to encompass the most likely range of truncated portions 302 of the patient 222 as shown in FIG. 3A. In another embodiment, the boundaries of the reconstruction mask 402' are dynamically determined at the time of reconstruction to be large enough to encompass the truncated portions 302 of the patient 222 as shown in FIG. 3A. In one embodiment the dynamic determination procedure consists of determining the boundaries 512-T, 512-B from the CT image before FOV extension or from the CT projection or localization image (using known CT system display features such as Scout View™ or Topogram™) used to plan the CT acquisition.

Figure 6:
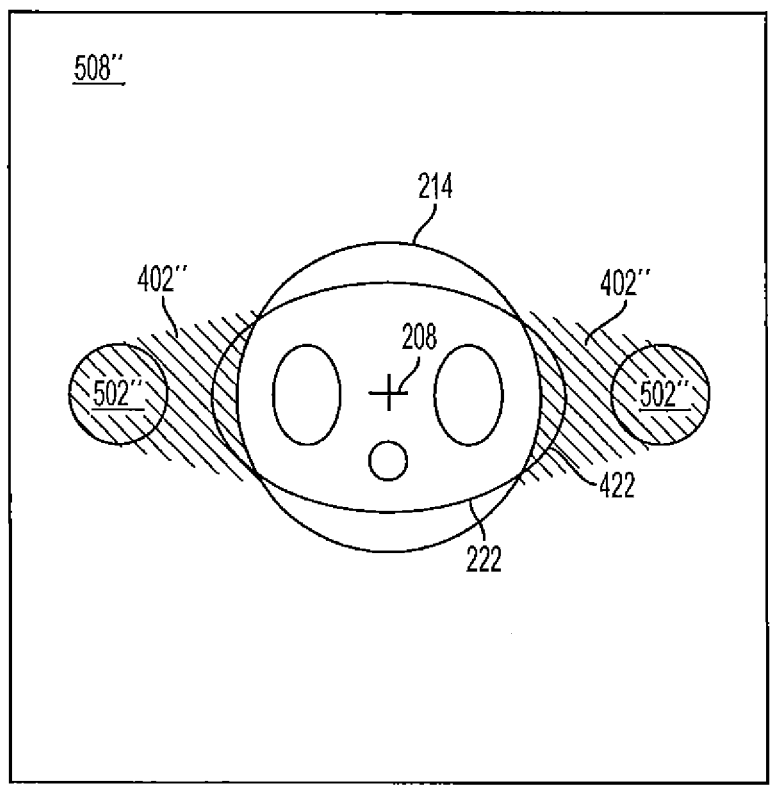
FIG. 6 shows yet another embodiment of a CT image reconstruction mask in accordance with the invention.

FIG. 6 illustrates a pictorial view of yet another embodiment of a CT image reconstruction mask 402". This embodiment of the image reconstruction mask 402" includes areas of interest 502" and areas of no interest 508". The areas of interest 502' encompass the truncated portions 302 of the patient 222 as shown in FIG. 3A and the area immediately surrounding those areas 302 as shown in FIG. 3A. By limiting the reconstruction mask to the areas of interest 502', the computational overhead is reduced further compared to the reconstruction mask 402' illustrated in FIG. 5.

The side boundaries of the reconstruction mask 402" illustrated in FIG. 6 extend from the sides of the image center 214 to areas corresponding to the lateral extent of the patient. The boundaries of the image reconstruction mask 402" are fixed at a position determined to encompass the most likely range of truncated portions 302 of the patient 222 as shown in FIG. 3A. In another embodiment, the boundaries of the reconstruction mask 402" are dynamically determined at the time of reconstruction to be large enough to encompass the truncated portions 302 of the patient 222 as shown in FIG. 3A. In one embodiment, the dynamic determination procedure involves determining the boundaries of mask 402" from a PET or SPECT image corresponding in axial position to the CT image. In one embodiment, the PET or SPECT image is supplied by one component of a PET/CT or SPECT/CT system and the boundaries of the reconstruction mask 402" are determined from the PET or SPECT image by image processing techniques known in the art such as thresholding.

Figure 7:
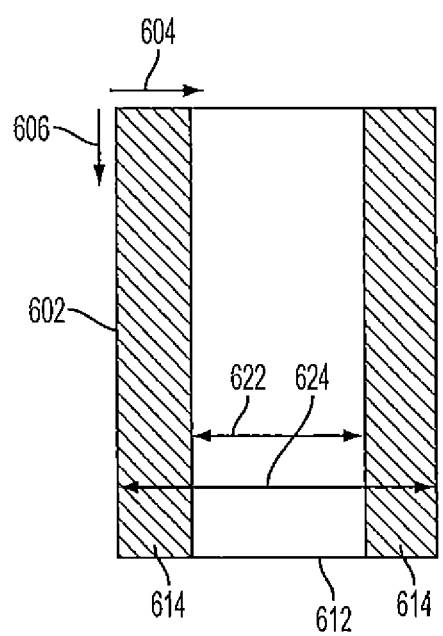
FIG. 7 shows one embodiment of a projection data mask in accordance with the invention.
Figure 8:
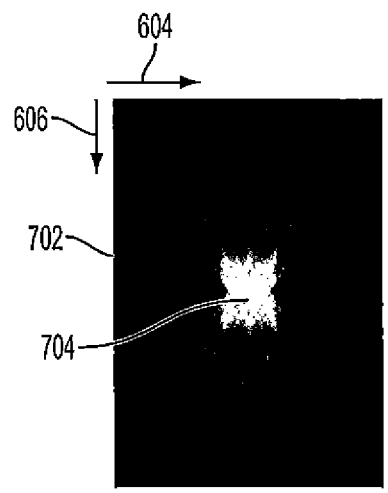
FIG. 8 shows an example of raw projection data obtained from a CT scanner.

FIG. 7 illustrates a pictorial view of one embodiment of a projection data mask 602 obtained by forward projecting the CT image reconstruction mask 402 as shown in FIG. 4. Forward projection is known in the art. FIG. 8 illustrates a pictorial view of one example of projection data 702 from a CT scanner 10a. In one embodiment the FOV extension system applies the projection data mask 602 illustrated in FIG. 7 to the raw projection data 702 illustrated in FIG. 8.

The projection data 702 along the x-axis 604 of the projection data mask 602 represent the samples, or data, seen by the detectors 204 with the source 202 and detectors 204 at one position relative to the patient 222 as shown in FIG. 2. The projection data 702 along the y-axis 606 represent the samples, or data, seen by the detectors 204 as the source 202 and detectors 204 rotate around the patient 222. The measured projection data 704, shown as different levels of gray in the black background of the projection data 702, is a 360° representation of one slice of the patient 222, as seen by the detectors 204 as they rotate around that part of the patient 222.

Referring to FIG. 7, the image center 214 is mapped to the center strip 612 of the projection data mask 602. Surrounding the center strip 612 are the truncated strips 614, which represent the portion of the projection data 702 outside the image center 214. In a typical CT scanner 10a, the width 622 of the center strip 612 representing the image center 214 is 50 cm and the total width 624 of the projection data mask 602 is on the order of 70 cm.

Figure 9A:
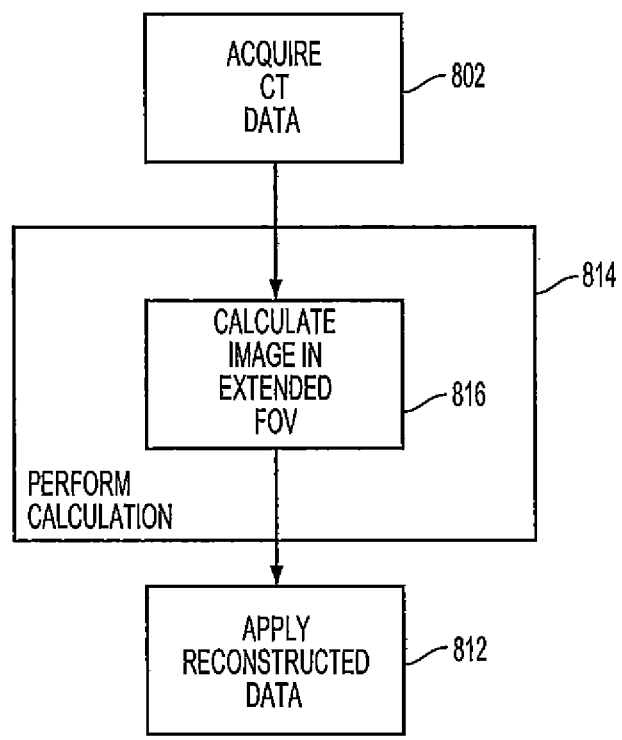
FIG. 9A is a flow diagram illustrating one example process for extending the effective FOV of a CT scanner in accordance with the present invention.
Figure 9B:
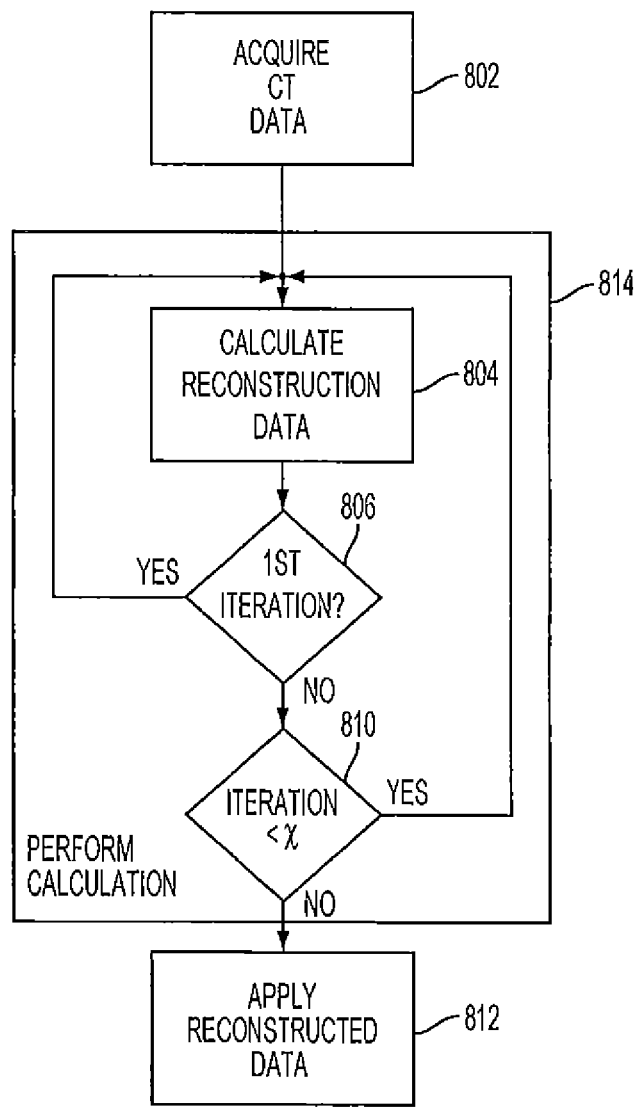
FIG. 9B is a flow diagram illustrating a second example process for extending the effective FOV of a CT scanner in accordance with the present invention.

FIGS. 9A and 9B illustrate example procedures of extending the effective FOV 214 of a CT scanner 10a in accordance with the present invention, wherein like reference numerals indicate like processes. The first step 802 is to acquire the CT projection data for all projection angles around a patient. The second major step 814 is to perform calculations that produce the reconstructed data in the region of the extended FOV. The last step 812 is to apply the reconstructed data either to obtain CT images, which can be used in co-registration with NM emission data, or to obtain attenuation correction factors for the NM emission data, or both. FIG. 9A illustrates an embodiment in which the FOV extension is performed with direct inversion of the projection data. FIG. 9B illustrates another embodiment in which the FOV extension is performed with iterative calculations.

FIG. 9A illustrates an embodiment of the present invention in which the calculation process 814 for obtaining the reconstructed data λ in the region of the extended FOV consists of directly inverting the projection data in a single step 816 as $$\lambda = (A^{-1}y)m + \lambda'(1-m)$$

where
λ' is the original CT image,
m is the image mask,
$A^{-1}$ is the inverse of the system matrix, and
y is the measured projection data.

The system matrix, which relates the image data to the projection data, is well-described in the art and will not be further discussed herein. $A^{-1}$ is a matrix whose elements can be computed by several methods known in the art including singular value decomposition. The image mask m is a matrix as well with the same dimensions as the final CT image λ and the original CT image λ'. This method of computing the FOV extension has the least computational overhead if the matrix m has a large number of elements whose values are zero, that is, if the image mask is small.

FIG. 9B illustrates an embodiment of the present invention in which the process 814 of obtaining the reconstructed data in the region of the extended FOV consists of iterative steps 804, 806, and 810. At step 804, image reconstruction data is calculated from the acquired CT projection data. At step 806, it is determined whether the reconstruction data calculation was a first iteration. If so, the reconstruction data is re-calculated using the first iteration calculation result with the acquired projection data to obtain a second iteration result. This process is repeated until a predetermined number of iterations x have been performed as determined at step 810, at which time the last iteration result is used as the final image reconstruction data. Alternatively, calculation of reconstruction data is repeated until the latest calculated estimate of the image, $\lambda^{n+1}$, is within a pre-selected tolerance or error level as compared to the immediately previous calculated estimate of the image, $\lambda^n$.

Step 804 can be any iterative reconstruction algorithm as known to those skilled in the art. Iterative reconstruction methods for CT images known in the art include ART (Algebraic Reconstruction Techniques), EM (Expectation Maximization), ML (Maximum Likelihood), MLTR (ML Transmission), MAP (Maximum A Priori), and OSEM (Ordered Subset Expectation Maximization). OSEM is a modified EM technique based on ordered subsets of projection data. For example, in accordance with the invention step 804 may take the form of the EM iterative reconstruction algorithm. In that case the calculation performed in the step of calculation 804 would be $$\lambda^{n+1} = \lambda^n m \frac{1}{BP(N)} BP\left(\frac{y}{FP(\lambda^n)}\right) + \lambda^0 (1-m)$$

for n=0 to a finite number of iterations, and where
$\lambda^{n+1}$ is the calculated estimate of the image,
$\lambda^n$ is the previously calculated estimate of the image,
$\lambda^0$ is the original CT image,
m is the image mask,
N is the normalized projection data mask,
y is the measured projection data,
BP is a back projection operator, and
FP is a forward projection operator.

The calculated estimate of the reconstructed image, $\lambda^{n+1}$, includes two parts as represented by the above equation. One part is the portion of the image overlaid by the reconstruction mask (e.g., 402, 402', or 402") and the other part is the original CT image contained within the image center or original FOV 214 and inside the inner boundary of the masks 402, 402', and 402".

The step of performing iterative calculations 804 begins with the original CT image, $\lambda^0$ or $\lambda'$. The original CT image, in one embodiment, is an image that has been processed with prior art methods of reconstructing the CT image. The prior art includes other methods of extending the FOV of the CT scanner. Such an image provides the baseline from which the present invention creates a CT image with an extended FOV. In another embodiment, the original CT image is the image as it is captured by the CT scanner 10a.

The image mask, m, is the portion of the image that is to be reconstructed. FIGS. 4, 5, and 6 illustrate image reconstruction masks 402, 402', and 402" representative of the image mask, m. In one embodiment, the reconstruction mask 402 is the portion of the CT image that is not within the image center 214. In another embodiment, the reconstruction mask 402' is a portion of the CT image adjacent the sides of the image center 214 not above or below the patient. In yet another embodiment the image mask 402" is a portion of the CT image outside of the CT scanner FOV 214 and within the boundary of the patient determined by the corresponding PET or SPECT image. By using a smaller image mask, m, the processing (and updating) are restricted to regions of interest, for example, the shoulders and arms of a patient that extend past the FOV of the scanner.

The normalized projection data mask, N, is represented by the projection data mask 602 illustrated in FIG. 7. In particular, N is represented by the two areas illustrated in FIG. 7, namely, the center strip 612 representing the image center (FOV) 214 or the center of the mask 402 and the truncated strips 614 representing the image outside the image center (FOV) 214 or outside the center of the mask 402.

The measured projection data, y, is the data from the CT detectors 14a, 204, an example being the projection data 702 illustrated in FIG. 8. The measured projection data, y, are unique to each image that is acted upon by the FOV extension system.

The back projection operator, BP, is the function for determining the image by using a back projection method. The back projection calculation of CT images is known in the art. The forward projection operator, FP, is the function for determining the image by using a forward projection method. The forward projection calculation of CT images is known in the art.

In another embodiment of reconstruction calculation process 804, the OSEM algorithm may be employed. It will be thus recognized by those skilled in the art that the scope of the present invention is not limited to any one iterative algorithm but to the contrary can be used with any suitable CT image reconstruction algorithm.

A characteristic of the FOV extension system calculation is that the summed forward projections are constant over the views. That is, there is no variation in the sum of the forward projection units for each view when compared to the other views.

In various embodiments in which the FOV extension system is used in conjunction with a SPECT or PET scanner 10b, the CT image is further manipulated to match the resolution of the PET image. The resolution of common CT scanners 10a is on the order of 0.1 to 1 millimeter. The resolution of common PET scanners 10b is on the order of 2 to 8 millimeters. To match the resolution of the PET scanner 10b for the purpose of attenuation correction, in one embodiment the calculated estimate of the reconstructed image, $\lambda$ or $\lambda^{n+1}$, has the same resolution as the PET image 10b by reducing the resolution of the original CT image to match that of the PET scanner 10b. This reduction in resolution occurs before performing the iterative calculations. In this embodiment, less computation is required for performing the iterative calculation. In another embodiment, the calculated estimate of the reconstructed image, $\lambda$ or $\lambda^{n+1}$, is calculated at the full resolution of the CT image and the calculated estimate has its resolution reduced to match that of the PET scanner 10b.

As used herein, the processor 22a, 22b should be broadly construed to mean any computer or component thereof that executes software. The processor 22a, 22b includes a memory medium that stores software, a processing unit that executes the software, and input/output (I/O) units for communicating with external devices. Those skilled in the art will recognize that the memory medium associated with the processor 114, 118 can be either internal or external to the processing unit of the processor without departing from the scope and spirit of the present invention.

In one embodiment the CT and SPECT or PET processors 22a, 22b are general purpose computers, in another embodiment, it is a specialized device for implementing the functions of the invention. Those skilled in the art will recognize that the processor 22a, 22b includes an input component, an output component, a storage component, and a processing component. The input component receives input from external devices, such as the CT detectors 14a and the SPECT or PET detectors 14b. The output component sends output to external devices, such as the other processor 22a, 22b, display devices, and data storage devices. The storage component stores data and program code. In one embodiment, the storage component includes random access memory. In another embodiment, the storage component includes non-volatile memory, such as floppy disks, hard disks, and writeable optical disks. The processing component executes the instructions included in the software and routines.

In one embodiment, each of the functions identified in FIGS. 9A and 9B are performed by one or more software routines executed by one or both of the CT and SPECT or PET processors 22a, 22b. In another embodiment, hardware performs one or more of the identified functions, and one or more software routines, run by one or both of the CT and SPECT or PET processors 22a, 22b, perform the remainder of the functions. In still another embodiment, the functions are implemented with hardware, with the processor 22a, 22b providing routing and control of the entire integrated system.

The CT and SPECT or PET processors 22a, 22b execute software, or routines, for performing various functions. These routines can be discrete units of code or interrelated among themselves. Those skilled in the art will recognize that the various functions can be implemented as individual routines, or code snippets, or in various groupings without departing from the spirit and scope of the present invention. As used herein, software and routines are synonymous. However, in general, a routine refers to code that performs a specified function, whereas software is a more general term that may include more than one routine or perform more than one function.

From the foregoing description, it will be recognized by those skilled in the art that a process and system for extending a CT FOV, from a truncated transmission scan of an imaged object, and its components have been described herein. This system includes apparatus and methods for performing iterative calculations for estimating a reconstructed image from a set of truncated CT projection data.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A method for extending the effective FOV of a CT scanner, comprising the steps of:
   a) defining a projection data mask for CT transmission data to be acquired as CT projection data;
   b) defining a reconstruction mask for acquired CT projection data surrounding a FOV of said CT scanner to be used in calculating image reconstruction data; and
   c) performing a reconstruction data calculation using said CT projection data defined by said projection data mask and said reconstruction mask to obtain image reconstruction data for reconstruction of a CT image, wherein the calculation uses the image mask and an image center as one boundary, and wherein said iterative reconstruction data calculation comprises solving an equation in the form of:

$$\lambda^{n+1} = \lambda^n m \frac{1}{BP(N)} BP\left(\frac{y}{FP(\lambda^n)}\right) + \lambda^0 (1-m)$$

for n=0 to a finite number of iterations, and where
$\lambda^{n+1}$ is the calculated estimate of the image,
$\lambda^n$ is the previously calculated estimate of the image,
$\lambda^0$ is the original CT image,
m is the image mask,
N is the normalized projection data mask,
y is the measured projection data,
BP is the back projection operator, and
FP is the forward projection operator.

2. The method of claim 1, wherein the calculation is performed by direct inversion of the projection data.

3. The method of claim 1, wherein the calculation is performed by an iterative reconstruction data calculation.

4. The method of claim 3 wherein said iterative reconstruction data calculation is performed for a pre-selected number of iterations.

5. The method of claim 3, wherein said iterative reconstruction data calculation is performed until a calculation result is within a pre-selected tolerance level of a preceding calculation result.

6. The method of claim 2, wherein said projection data mask includes projection data in a predetermined area surrounding said FOV.

7. The method of claim 2, wherein said reconstruction mask includes projection data from truncated areas in said predetermined area surrounding said FOV.

8. The method of claim 3, wherein said projection data mask includes projection data in a predetermined area surrounding said FOV.

9. The method of claim 3, wherein said reconstruction mask includes projection data from truncated areas in said predetermined area surrounding said FOV.

10. The method of claim 1, further comprising the step of using said CT image reconstruction data to develop attenuation correction factors for PET projection data acquired from the same object as said CT projection data.

11. The method of claim 1, further comprising the step of co-registering said CT image reconstruction data with PET reconstruction data pertaining to the same object as said CT image reconstruction data.

* * * * *